(12) United States Patent
Caiazza (10) Patent No.: US 11,951,012 B2
(45) Date of Patent: Apr. 9, 2024

(54) FEMORAL ELEMENT OF KNEE SPACER (71) Applicant: Cossington Limited, Kingston upon Thames (GB)

(72) Inventor: Emanuele Caiazza, Rome (IT)

( * ) Notice: Subject to any disclaimer, the term of this patent is extended or adjusted under 35 U.S.C. 154(b) by 0 days.

(21) Appl. No.: 17/813,049

(22) Filed: Jul. 18, 2022

(65) Prior Publication Data

US 2024/0016617 A1    Jan. 18, 2024

(51) Int. Cl.
*A61F 2/38* (2006.01)
*A61F 2/30* (2006.01)

(52) U.S. Cl.
CPC ........ *A61F 2/3859* (2013.01); *A61F 2/30734* (2013.01); *A61F 2002/30131* (2013.01); *A61F 2002/30672* (2013.01)

(58) Field of Classification Search
CPC ..... A61F 2/3859; A61F 2/389; A61F 2/30734
See application file for complete search history.

(56) References Cited

U.S. PATENT DOCUMENTS

| | | | |
|---|---|---|---|
| 2012/0271428 A1* | 10/2012 | Heldreth | A61F 2/3836 623/20.31 |
| 2022/0273450 A1* | 9/2022 | Steines | A61F 2/30942 |

\* cited by examiner

*Primary Examiner* — Jason-Dennis N Stewart
(74) *Attorney, Agent, or Firm* — Themis Law (57) ABSTRACT

A femoral element for a spacer device for a knee joint.

17 Claims, 3 Drawing Sheets

FEMORAL ELEMENT OF KNEE SPACER

FIELD OF THE INVENTION

The present invention relates to a femoral element for a spacer device for the knee joint, as well as to a spacer device for the temporary replacement of knee joint prostheses which must be removed, for example following the onset of an infection.

BACKGROUND OF THE INVENTION

In the field of implantology of joint prostheses, it is known that joint prostheses can be susceptible of removal for various reasons, in particular for local infections of the joint after the implant of the prosthesis.

In such case, it is not possible to immediately substitute the infected prosthesis with a new prosthesis, given that the site of the joint must be treated using suitable antibiotic medications. During the period required for the antibiotic treatment, it is important to maintain the articular space necessary for the implant of a new prosthesis, thus preventing the shortening of the tissues, the atrophying of the joint and the loss of muscle tone. Such technique is known as "two-step implantation" of the joint prostheses.

Temporary articular spacer devices for the knee are known, manually made by the surgeon during the spacer implant surgical operation. Such spacer devices are made of bone cement and are suitably shaped, in a manual manner, immediately before the implant in the articular site.

On the market spacer devices for joints preformed and to be implanted without requiring a manual forming during the surgical operation are available.

Nevertheless, such devices have the drawback of being composed of a femoral part and a tibial part having standard sizes and combined with each other a priori, which are thus not always easily adaptable to the anthropomorphic sizes of each patient.

One consequence of the incorrect adaptability of the known spacer devices to the anthropomorphic size of the patient lies in the impossibility of ensuring good mobility of the joint as well as a good resistance of the spacer device itself to the stresses, in particular lateral, to which it is normally subjected during use. It follows that the patient has a poor quality of life while waiting for a new joint prosthesis, and therefore there is the need for a spacer device for joints of the human body which overcomes the aforesaid drawbacks.

The international application published under number WO2018015878A1 teaches a modular spacer device for the knee joint comprising a tibial element that can be attached to a tibial bone as well as a femoral element that can be attached to a femoral axis and in articulation engagement with the tibial element.

Moreover, the femoral element has a surface of articulation to the tibial element, which is convex and laterally has a curved profile of the "ammonite" type with a radius of curvature increasing from a rear section to a front section.

If this spacer device, on the one hand, ensures good performance, considering the specific configuration, it cannot be easy extracted from a respective mold.

SUMMARY OF THE INVENTION

Therefore, the main purpose of the present invention is to improve the state of the art with regard to spacer devices for the knee joint of the human body.

Another object of the present invention is to provide a new femoral element for a spacer device which is effective and moldable in a simple and rapid manner.

A further main object of the present invention is to provide a femoral element as indicated above which can be molded and which is adaptable to the anthropomorphic measurements of each patient to which it is applied.

In accordance with an aspect of the present invention, a femoral element is provided for the knee joint according to claim 1.

In accordance with another aspect of the present invention, a spacer device for the knee joint according to claim 17 is provided.

The dependent claims refer to preferred and advantageous embodiments of the invention.

BRIEF DESCRIPTION OF THE DRAWINGS

Further characteristics and advantages of the present invention will become more evident from the detailed, non-exclusive description of a preferred embodiment of a femoral element and of a knee spacer device according to the present invention, given by way of not limitative example, in the enclosed drawings tables in which.

DETAILED DESCRIPTION OF EMBODIMENTS OF THE INVENTION

For the description of a femoral element and a spacer device, with the aim of better explaining the structure of the present invention, we will refer to planes and axes of symmetry of the human body in which they are implanted and as a function of how (in what position and with which relative arrangement) they are implanted, such as one or more of the following:

the front plane, which is the vertical plane in which, considered a person in an upright position, a direction from one side to the other of the person lies and intercepts, for example, the person's body at half its thickness, the sagittal plane, which is the vertical plane in which, considered a person in an upright position, a direction from the front to the rear lies of the person and intercepts, for example, the person's body at half its width, the transverse plane, which is the horizontal plane, which, considered a person in an upright position, intercepts, for example, the person's body at waist height, the craniocaudal axis, which is the vertical axis, which, considered a person in an upright position, intercepts, for example, the person's body at half its thickness and half its width, the sagittal axis, which is the horizontal axis and in the direction from the front to the rear of the person, which, considered a person in an upright position, intercepts, for example, the person's body at half its width, the latero-lateral axis, which is the horizontal axis and from one side to the other of the person, which, considered a person in an upright position, intercepts, for example, the person's body at half its thickness.

Furthermore, indications such as "rear", "front" or the like are clearly to be interpreted in relation to the positioning of a femoral element or spacer device in a human body in an upright position, for which, for example, a rear component or section is that, in use, placed on the back of the knee or closer to the back or rear part of the knee.

With reference to the enclosed figures, a femoral element 1 for a spacer device 2 for the knee joint is shown, which femoral element 1 is designed to be constrained to a femoral bone and has a substantially "C" plan configuration, wherein each free end of the "C" delimits a condylar portion or posterior lobe 4 of the femoral element.

A device according to the present invention is foreseen for being implanted in a bone or joint site of a knee of a human body, for example for replacing an infected prosthesis.

The spacer device is "temporary" in the sense that, once it has performed its function of healing and maintaining the space of the bone or joint site, it will be removed from the knee joint and replaced, for example, with a permanent prosthesis.

In this regard, a spacer device performs a function of maintaining joint spaces as well as treating bone infection by releasing a quantity of antibiotic or a pharmaceutical or medical substance in the infected zone. Regarding this aspect, a spacer can cure an infection in progress by releasing a pharmacological substance, such as an antibiotic in a targeted manner and in infinitesimal quantities, while the application of even high doses of antibiotic, but with methods that do not provide for the use of spacers, such as washing the infected place with high-dose antibiotic solutions, does not allow the same results to be obtained.

Moreover, the femoral element 1 has a first surface 5 of articulation or engagement, for example by rotation and/or translation, which surface faces, in use, towards a tibial element 3 for articulating the femoral element 1 on or with a tibial element 3 or on or with a surface thereof, and a second surface 6 opposite to it for attachment to a femoral bone by means of a suitable fluid or compound.

It is then noted that the first surface 5 has at the rear or at each of the posterior lobes or condylar portions 4 a terminal section or rear terminal section 5a opening or extending up to the free or terminal edge 4a of the posterior lobes or condylar portions 4, which terminal section 5a is substantially straight and extends so as to be, in use, substantially parallel to the craniocaudal axis or slightly inclined with respect to the latter, for example between 0 and 10° or between 0 and 5° or between 0 and 3° with respect to the latter.

Of course, this expression means that the terminal section 5a is substantially parallel or lies in the frontal plane or in any case defines an angle between 0 and 10° or between 0 and 5° or between 0 and 3° with the latter, with the terminal end at the free edge 4a at a distance from the front of the femoral element 1 greater than the base end in common with an adjacent and subsequent section of the first surface 5.

As an alternative, the terminal section 5a is slightly curved, but with a radius of curvature very large and remarkably greater than that of, for example at least 3/2 or double or triple with respect to, an adjacent and subsequent section of the first surface 5, for example the rear section which will be better discussed later.

Thus, for example, the terminal section 5a could have a radius of curvature even greater than 20, 30, 40, 50 or 60 mm, while the respective center of curvature could be between the terminal section 5a and the front of the femoral element 1 or even beyond the latter, with a suitable position along the craniocaudal axis, for example substantially at the same level of the centers of curvature of the other sections of the first surface 5 or also at different levels.

Advantageously, the terminal section 5a extends from the free or terminal edge 4a of each of the condylar portions 4 for an extension equal to at least 60%, 70%, 80% or 90% of the latter.

Basically, the terminal section 5a has two lengths Sa1, 5a2, one for each posterior lobe or condylar portion 4.

If desired, the terminal section 5a extends from the free or terminal edge 4a of the condylar portions 4 for an extension equal to about 15-20 mm, for example about 18-19 mm.

Preferably, the condylar portions 4 have a free or terminal edge 4a with an upper, in use, surface 4a1, which is substantially straight and with a main extension dimension aligned or parallel to the latero-lateral axis, if desired extending in the transversal plane or parallel to the latter.

Still more preferably, the upper surface 4a1 is straight for an extension equal to at least 60%, 70%, 80% or 90% of the width or maximum dimension in direction of the latero-lateral axis of the condylar portions 4.

With regard to this aspect, the width or dimension in the direction of the latero-lateral axis of the condylar portions 4 is substantially constant or increases in the direction of moving away from the upper surface 4a1 for less than 30% or 20% or 10%.

Advantageously, each free or terminal edge 4a is provided with a main upper surface 4a1 and then with two front and rear connection portions 4a2, 4a3, if desired with a rounded profile, one for connection or continuation with the main terminal section 5a and the other for connection or continuation with a rear section of the second surface 6.

Lateral portions 4a4, 4a5 can then be provided, even the same if desired with a rounded profile, for connection of each free or terminal edge 4a with the flanks or sides of the condylar portions 4.

Advantageously, the first surface 5 of the femoral element 1 is convex for all or part of its extension, naturally, with a convexity facing, in use, towards the respective femoral bone, and has a curved profile substantially of the nail type in the sagittal plane or parallel to it with a front section 5b having a first radius of curvature R1, at least one central section 5c having a second radius of curvature R2 smaller or larger than the first radius of curvature R1, and then at least one rear section 5d having a third radius of curvature R3 smaller or larger than the first R1 and/or the second R2 radius of curvature. Of course, the sections 5b, 5c and 5d are one continuation of the other.

Clearly, the convexity could involve the sections 5b, 5c, 5d and, if desired, but not necessarily, also the terminal section 5a.

The radii of curvature R1, R2 and R3 are shown in a simplified manner in the figures with reference to the respective circumference, but it will be understood that the same are the radii of the latter.

Of course, moving along a latero-lateral axis, in planes parallel to the sagittal plane, the configuration of the first surface 5 preferably remains substantially constant or changes in proportions, but preferably not in the overall configuration, clearly taking into account the posterior C-configuration and, as will also be said later, of the fact that it could define centrally a central channel 14.

In this case, the terminal sections 5a can extend from the rear end 5d1 of the rear section 5d of the first surface 5.

Moreover, a curved or straight front terminal section 5e of the first surface could be provided, at the front of the femoral element 1, which constitutes the front continuation of the front section 5b.

If desired, the distance H1 along or parallel to the sagittal axis of the center of rotation CR1 of the first radius of curvature R1 from the center of rotation CR2 of the second radius of curvature R2 is equal to about 1-3 mm, for example about 1.5 mm.

The distance H2 along or parallel to the craniocaudal axis of the center of rotation CR1 of the first radius of curvature R1 from the center of rotation CR2 of the second radius of curvature R2 can be approximately 2-6 mm, for example 3.7 mm.

According to a non-limiting example, the distance H3 along or parallel to the sagittal axis of the center of rotation CR1 of the first radius of curvature R1 from the center of rotation CR3 of the third radius of curvature R3 is equal to about 15-20 mm, for example 18.5 mm.

If desired, the distance H4 along or parallel to the craniocaudal axis of the center of rotation CR1 of the first radius of curvature R1 from the center of rotation CR3 of the third radius of curvature R3 is approximately 20-26 mm, if desired, approximately 23.4 mm.

With reference to the dimensions of any radii of curvature:

the first radius of curvature R1 could for example be between about 35 and about 45 mm, the second radius of curvature R2 could for example be between about 40 and about 50 mm, and/or the third radius of curvature R3 could for example be between about 10 and about 15 mm.

By way of non-limiting example:

the front section 5b has an extension between 10% and 60% of the extension of the first surface 5 not considering the terminal section 5a, for example between 20% and 40%, and/or the central section 5c has an extension between 10% and 60% of the extension of the first surface 5 not considering the terminal section 5a, for example between 20% and 40%, and/or the rear section 5d has an extension between 5% and 30% of the extension of the first surface 5 not considering the terminal section 5a, for example between 5% and 20%.

According to a non-limiting variant, at the second surface 6 at least one recess zone 7-12 is delimited, which is designed to facilitate the adhesion of the femoral element 1 to the corresponding femoral bone end, by means of a filling or constrain material or fluid, specifically bone cement and/or any other suitable material, during the surgical procedure of implantation of the spacer device 3.

If desired, this recessed zone 7-12 is open towards a respective side, medial or lateral, of the femoral element 1, so as to facilitate the escape of fluid, such as bone cement, of constraining to a femoral bone, that should be applied in excess.

At least one recessed zone 7-12 can have an extension in plan, much greater than the respective depth.

In this regard, at least two rear recessed zones 7, 8 could be provided with L-shaped configuration and each with a first branch 7a, 8a opening towards a respective side, medial or lateral, of the femoral element 1 and a second branch 7b, 8b opening towards the top of the femoral element 1 and delimited in a respective condylar portion 4 of the femoral element 1. In this case, the first branch 7a, 8a can have an extension between about ¼ and ½ the width (latero-lateral axis) of the femoral element.

Alternatively or in addition to what has now been indicated, at least two median recessed zones 9, 10 each opening towards a respective side, medial or lateral, of the femoral element 1 can be provided.

Alternatively or in addition to what has now been indicated, at least two front recessed zones 11, 12 could be provided with L-shaped configuration and with a first branch 11a, 12a opening towards a respective side, medial or lateral, of the femoral element 1 and a second branch 11b, 12b opening towards the top of the femoral element 1 and delimited in the front portion of the femoral element 1. In this case, the first branch 11a, 12a can have an extension between about ¼ and ½ the width (latero-lateral axis) of the femoral element 1.

If desired, the second surface 6 of the femoral element 1 is concave and has in the sagittal plane or parallel to it a curved profile of the "U" type comprising at least an anterior section 6a, 6b curved or with straight thicknesses inclined or curved with respect to the craniocaudal axis, then an intermediate or base section 6c substantially parallel to the sagittal axis and then a posterior section 6d parallel or slightly inclined with respect to the craniocaudal axis. The posterior section 6d has two parallel segments or portions each defining the interior of a respective posterior lobe or condylar portion 4.

As regards in particular the front section 6a, 6b, according to the non-limiting embodiment illustrated in the figures, it can have two segments 6a, 6b, one 6a inclined with respect to the other 6b.

Thus, for example, a first segment 6a of the front section can delimit an angle of about 90°-110°, if desired about 100° with respect to the intermediate or base section 6c, a second segment 6b of the front section can define an angle of about 130-140°, if desired about 135° with respect to the intermediate or base section 6c, while the rear section 6d can delimit an angle of about 90°-110° if desired about 100° with respect to the intermediate or base section 6c.

With such a configuration, each of the posterior lobes 4 of the femoral element 1 is delimited or defined between at least one posterior section 6d of the second surface 6 and the terminal sections 5a of the first surface 5.

The thickness of the femoral element 1 can be constant or even variable in the proximal-distal direction or craniocaudal axis.

By way of non-limiting example, a femoral element 1 according to the present invention can have:

external length H5, i.e., dimension in a sagittal plane from the front free edge to the posterior free edge of the first surface 5 equal to about 60-80 mm, for example about 70 mm, and/or internal length H6, i.e., dimension in a sagittal plane from the front free edge to the posterior free edge of the second surface 6 equal to about 45-55 mm, for example about 53-54 mm.

With regard to the height H7 of the posterior lobes or condylar portions 4, by way of non-limiting example, the free edge defining the same can be at a distance from the intermediate or base section 6c equal to about 15-25 mm, for example about 17-19 mm.

As for the height H8 of the front part of the femoral element, by way of example and not limiting, the free edge defining the same can be at a distance from the intermediate or base section 6c equal to about 25-35 mm, for example about 30 mm.

Finally, with regard to the length H9 (distance in a transverse plane between the anterior and posterior ends) and width H10 (distance in a transverse plane between the sides or flanks) of the femoral element 1, by way of non-limiting example, they can be respectively between 50 and 90 mm (length), if desired between 60 and 80 mm and between 60 and 100 mm (width), if desired between 70 and 90 mm.

Figure 1:
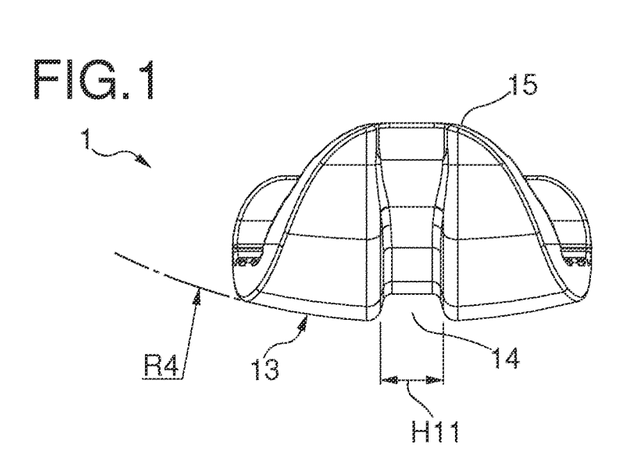
FIG. 1 is a front view of a femoral element for a spacer device according to the present invention.
Figure 2:
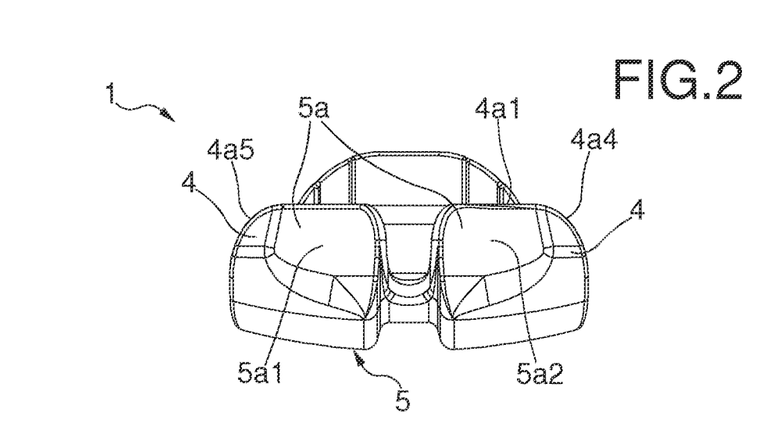
FIG. 2 is a rear view of the femoral element of FIG. 1.
Figure 3:
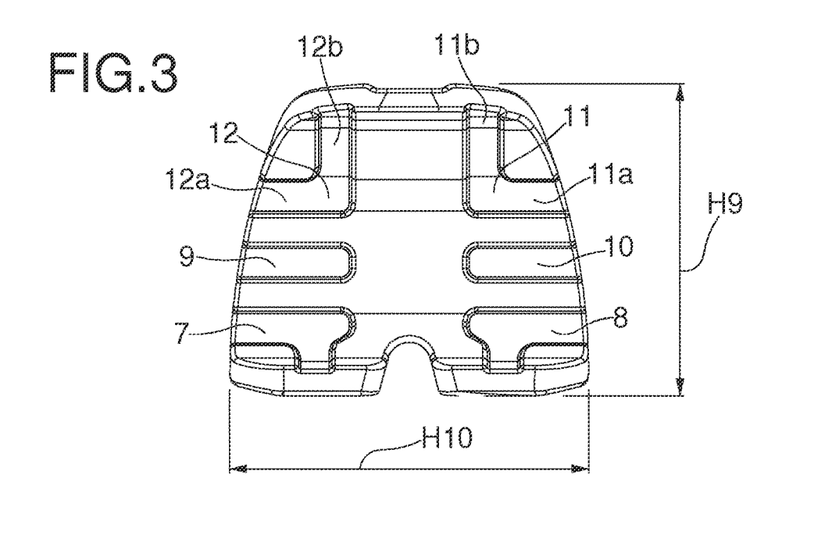
FIG. 3 is a top view of the femoral element of FIG. 1.
Figure 4:
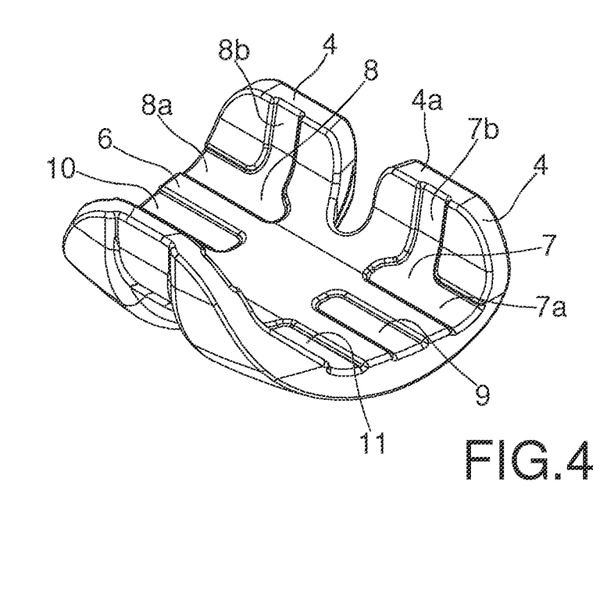
FIG. 4 is a perspective view slightly from above of the femoral element of FIG. 1.
Figure 5:
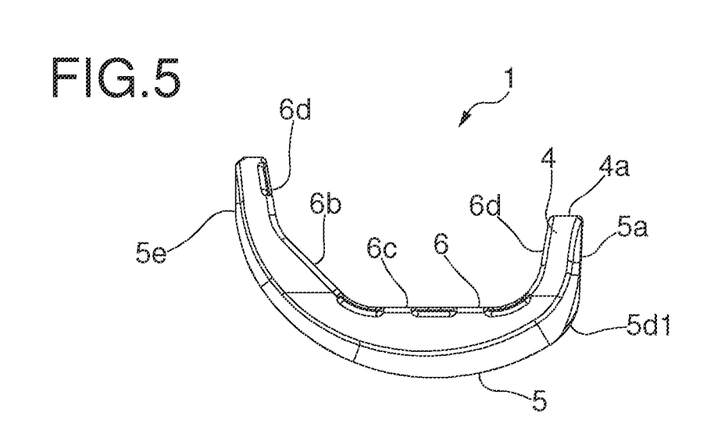
FIGS. 5 to 7 are lateral views of the femoral element of FIG. 1 each with respective indications.
Figure 6:
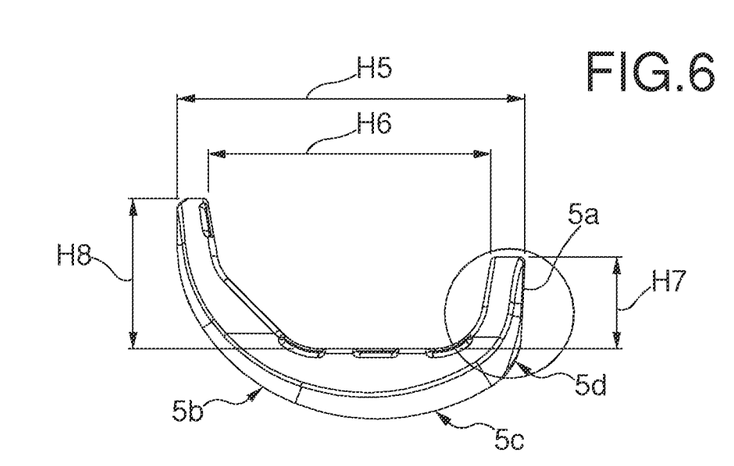
Figure 7:
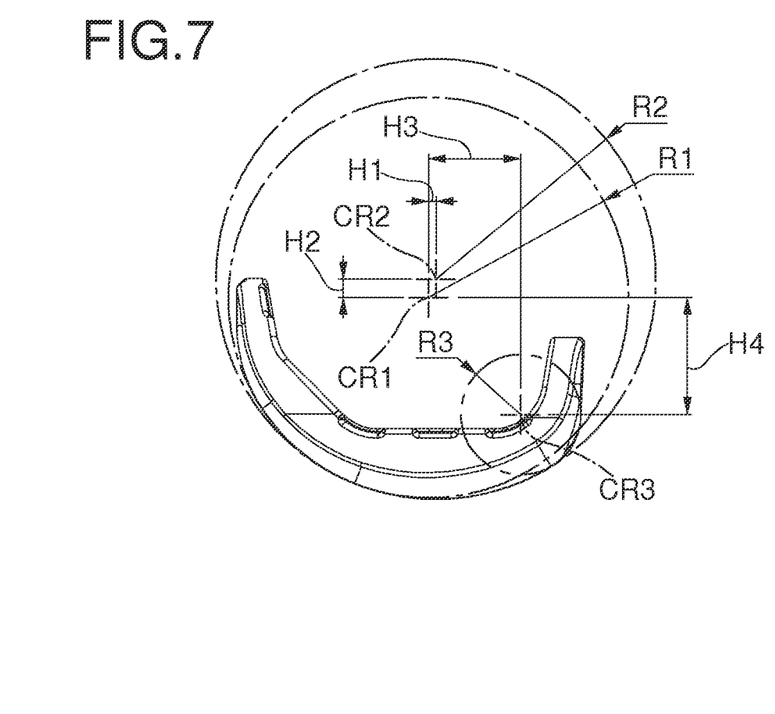
Figure 8:
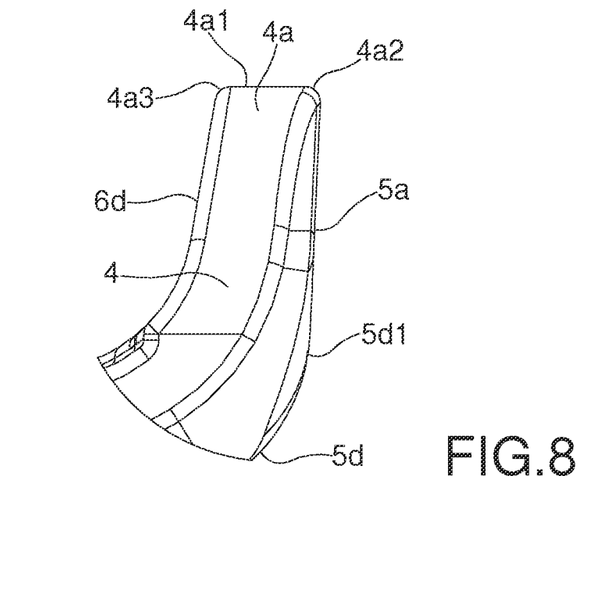
FIG. 8 is a view of a detail on an enlarged scale of FIG. 5.
Figures 9, 10, 11:
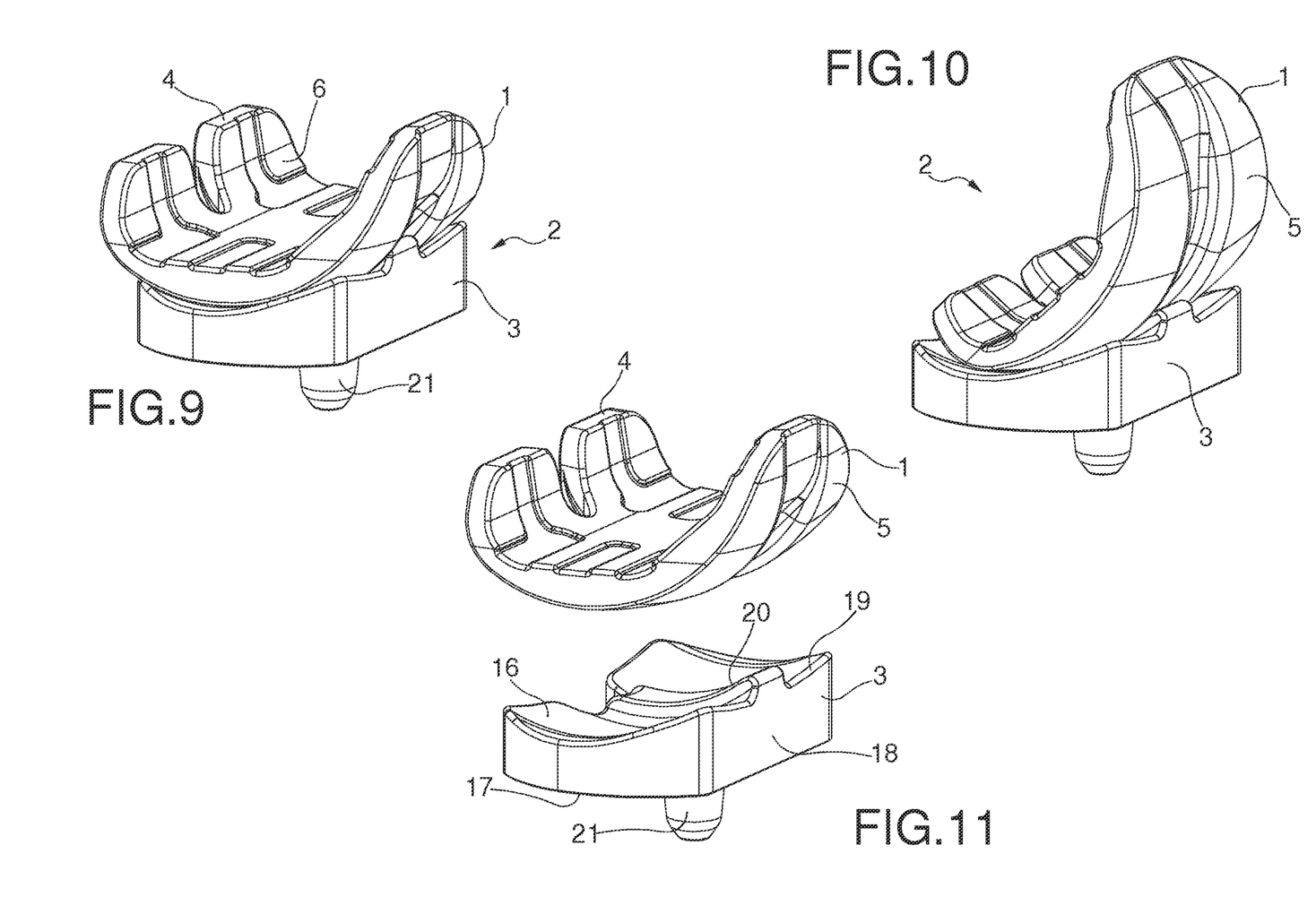
FIGS. 9 and 10 are slightly top perspective views of a spacer device according to the present invention in two respective operating positions.
FIG. 11 is an exploded view of the spacer device of FIGS. 9 and 10.

With reference to a view or section taken along a frontal plane, the femoral element 1 or better the first surface can have (see FIGS. 1 and 2) a substantially curved lower profile 13, more particularly convex, according to a fourth ray of curvature R4, for example between about 130 and 160 mm, if desired about 145-155 mm.

The first surface 5 of the femoral element 1 can also delimit a central channel 14, extending according to (but not parallel to) a sagittal axis of the femoral element 1, i.e. starting from the front section 5b towards the central section 5c and the posterior section 5d. This central channel 14 can be delimited by rounded edges of the femoral element.

By way of non-limiting example, the central channel 14 can have a width H11 between about 5 and about 30 mm, if desired, about 10-20 mm.

Frontally, the femoral element 1 has an edge or upper profile 15, which is substantially curved according to a substantially concave extension, in use, downward.

Clearly, this profile or upper edge could also be configured in a different way, for example inclined to the left or to the right.

The femoral element 1 according to the invention may, according to a variant not shown, have a raised element or central rib with an antero-posterior extension, rising centrally from the second surface. This central rib would be substantially aligned, in a sagittal plane, with the central canal 14.

A subject-matter of the present invention is also a spacer device comprising a femoral element 2 as well as a tibial element 3 suitable to be constrained to the tibial bone, at one end of the tibial bone facing the knee joint, which tibial element 3 comprises a first surface 16 facing, in use, towards the femoral element and designed to articulate or engage, for example by rotation and/or translation with the first surface 5 of the femoral element and a second surface 17 opposite to the first surface and for the constraint to the bone.

As regards the tibial element 3 of the spacer device according to the invention, it has a substantially inverted "U" plan configuration, in which the base portion of the "U" corresponds to a front, in use, section 18 of the tibial element 3 and is substantially straight.

According to an aspect of the present invention, the first surface 16 of the tibial element 3 is concave and has a laterally curved profile, more specifically concave, substantially complementary to the extension of the central section 5c of the corresponding femoral element 1.

This first surface 16, in one version of the invention, with reference to a view or section taken along a front plane, further has a substantially concave profile 19 corresponding to the lower profile 13 of the femoral element 1.

In a further version of the invention, the first surface 16 can have at the front a substantially flat or concave profile 19 but with a very large radius of curvature (for example much greater than the lower profile 13) such as to render it substantially flat. Even in this version, the first surface 16 acts as a support and articulates with the lower profile 13 of the femoral element 1.

Still, in a further version of the invention, the first surface 16 can have a profile 19 of the non-symmetrical type, in the sense that the profile 19, in its medial portion, can have a concave shape and in its lateral portion it can have a flat profile, or vice versa, depending on the specific anatomical needs of the patient. According to this version, the tibial element 3 has a "left" or "right" profile depending on the position of the concave portion. In all cases, the profile 19 ensures the support and articulation with the lower profile 13 of the femoral element 1.

Furthermore, the first surface 16 of the tibial element 3 may have a raised portion or central rib 20 with a rounded profile (as in the sense above described with reference to the central channel 14 of the femoral element). This raised portion or central rib 20 extends along a sagittal axis in the tibial element 3 and has a configuration that is substantially insertable to size or with slack in a corresponding central channel 14 delimited in the femoral element 1.

The central rib 20, as it will be easy to understand, acts as a stabilizing means in the sense that it prevents lateral displacements between the femoral element 1 and the tibial element 3, once they have been coupled together as described above. In any case, the central rib 20 and the central channel 14 are sized in such a way that there is a certain play between them, so that the femoral element 1 can move along the sagittal and/or latero-lateral axis with respect to the tibial element 3.

With such a configuration of the central rib 20 of the tibial element 3 and of the central channel 14 of the femoral element 1, the person skilled in the art will have no difficulty in understanding how the femoral element of the spacer device 2 according to the invention can be articulated on the corresponding tibial element 3. In fact, the femoral element 1, more particularly its first convex surface 5, in use can roll and partially translate with respect to the first concave surface 16 of the tibial element 3, while maintaining a high lateral stability due to the particular dimensioning of the central rib 20 and of the corresponding central channel 14.

This roto-translational motion is a consequence of the configuration of the femoral element 1 and of the corresponding configuration of the tibial element 3.

Going back to the tibial element 3 of the spacer device according to the invention, it can have the second surface 17 substantially flat and connected (in any suitable way), in a central region corresponding to the central rib 20 of the first surface 16, to an engagement means. This engagement means is used for coupling the tibial element 3 to a bone end of a patient.

The femoral 1 and/or tibial 3 elements can also include a stem 21 in one piece or connectable (removably or not) with the other portion (for example the one shown in the figures) of these elements 1 and 3.

Advantageously, the femoral element 1 and/or the tibial element 3 can have a different extension in plan according to various predetermined formats or sizes, but they always maintain constant (i.e. independent of the format or size) the configuration—i.e. the size and the shape—respectively of the possible central channel 14 and/or of the central rib 20, and/or of the radii of curvature.

This way, the tibial element 3 and the femoral element 1 of the spacer device according to the invention can always be coupled to each other at the respective first surfaces 16 and 5, regardless of their respective formats or sizes.

Moreover, the central rib 20 of the tibial element 3 and the central channel 14 of the femoral element 1 are configured in such a way that, if during the movement of the knee joint the device undergoes lateral thrust stresses, the central rib 20 maintains the femoral element 1 in place, ensuring correct movement and good joint stability.

The lateral stability of the spacer device according to at least one version of the invention is also further due to the particular convex profile of the first surface 5 of the femoral element 1 and the corresponding concave or "sunken" profile of the corresponding first surface 16 of the tibial element 3.

Advantageously, the different formats or sizes of the tibial element 3 and the femoral element 1 are interchangeable, so as to be adaptable to the anthropomorphic measurements of the femoral and tibial ends of each patient, which may differ from each other.

The configuration of the radii of curvature of the first surfaces 5 and 16 of the femoral 1 and tibial 3 element allow to obtain a prevalent motion of mutual rolling between the femoral 1 and tibial 3 element as well as a mutual translation or sliding motion.

As a function of this, the patient can perform a flexion and extension movement of the joint similar to the normal physiological movement of the knee joint.

In particular, the femoral element 1 is shaped in such a way as to be coupled with any size of the tibial element 3 to adapt the dimensions of the spacer device with the dimensions of the bone ends to which it must be connected.

With such a configuration, the above-described spacer device allows to obtain a high mobility of the knee joint and a movement similar to that of a natural joint, even in the presence of different anatomical measurements, between the different joint portions of a patient.

According to a further aspect of the invention, the tibial element 3, the femoral element 1 and, if provided, the stem are preformed in different formats or sizes and made of biologically compatible material, possibly porous.

According to another preferred aspect of the present invention, at least one zone in bas-relief or recess of extension, in plan, much greater than the respective depth is provided in the second surface 17 of the tibial element 3.

These bas-relief zones, in a completely identical way to that indicated for the femoral element 1, are provided to facilitate the adhesion of the tibial element 3 to the corresponding tibial bone end, using a filling material, specifically bone cement and/or any other suitable material during the surgical procedure of implanting the spacer device.

Their arrangement, as well as their extension, may vary according to specific needs, for example according to the format or size of the tibial element 3.

Any bas-relief zones both in the femoral element 1 and in the tibial element 3 form sites for housing a filling material referred to above, which, according to an aspect of the present invention, can be of the hardening or solidifiable type.

In one version of the invention, the filling material can be prepared by the surgeon during the operating procedure and/or it can be free of pharmaceutical or medical substances and/or can be added with them according to the choice of the surgeon and the needs of the patient.

In the event that the filling material also includes at least one pharmaceutical or medical substance, the bas-relief zones 7-12, if provided, act, in practice, as a reservoir for the storage of this pharmaceutical or medical substance to be released inside the human body, more particularly in the bone or joint site where the spacer device 2 is implanted.

Naturally, the pharmaceutical or medical substance, such as for example at least one antibiotic, inserted in the filling material is of the soluble type, and thus it is released towards the adjacent bone tissue or in contact with the filling material in order to heal or at least prevent its infection.

In one version of the invention, the filling material is non-absorbable or degradable in the human body at least for the time the spacer device remains inside the human body itself. Therefore, the filling material is permanent.

In one version of the invention, the filling material is applied by the surgeon before implanting the spacer device itself.

In a further version of the invention, the afore-mentioned filling material can thus comprise at least one pharmaceutical or medical substance already prepared in the material, which constitutes the filling material itself, and possibly it, during the preparation step, can be added with a further substance.

According to an aspect of the present invention, the filling material, by virtue of the preparation and solidification step to which it is subjected, can be porous.

The size of the pores of the filling material (and/or of the material with which the femoral element 1 or the tibial element 3 of the spacer device are made) is, in any case, such as to prevent the bone regrowth inside it and, thus, inside the spacer device 2 according to the invention, which spacer, as above mentioned, is temporary.

Such a configuration of the pores, thus, facilitates the subsequent removal of the spacer device itself from the treated bone or joint site, once its curative function has been performed.

By way of example, in one version the pores can have average dimensions of less than 100 microns.

The spacer device 2 is configured in such a way that when, in use, it is implanted in the human body, the filling material in the bas-relief zones 7-12 is in contact with the bone tissues to be treated.

According to one version, the filling material is flush with the respective second surface 6 and/or 17 of the respective femoral element 1 or tibial element 3.

According to a further version, the filling material goes out from the respective bas-relief zone 7-12 and thus it protrudes with respect to the second surface 6 and/or 17 of the respective femoral element 1 or tibial element 3.

As already mentioned above, the plan extension of each bas-relief zone 7-12 is much greater than the respective depth. This way, among other things, the application of the aforementioned filling material by the surgeon in these areas is facilitated.

According to a further aspect of the invention, the tibial element 3, the femoral element 1 and, if provided, the stem are preformed in different formats or sizes and made of biologically compatible material, possibly porous.

This biologically compatible material can be chosen among plastics, possibly thermoformable, such as polymethyl methacrylate (PMMA), polyvinyl chloride (PVC), polystyrene (PS), polyethylene (PE), ultra high molecular weight polyethylene (UHMWPE), high or low density polyethylene, etc., or non-polymeric materials, ceramics, metals, metal alloys, organo-metal compounds, and/or a combination thereof.

In one version of the present invention, the biologically compatible material is a bone cement based on polymethylmethacrylate (PMMA).

In another version of the invention, the afore-mentioned biologically compatible material is initially free of pharmaceutical or medical substances.

In a further second version, the afore-mentioned biologically compatible material comprises at least one pharmaceutical or medical substance.

According to a further version of the present invention, the biologically compatible material can be a ceramic cement, such as for example calcium sulphate known as gypsum or CaSO$_4$, which, in addition to solidifying in a short time, is capable of releasing calcium ions.

However, for the realization of the elements of the spacer device 1 according to the invention, additional biocompatible materials can be used, with respect to what is described above, without thereby departing from the scope of the present invention.

The above-described invention achieves numerous advantages.

First of all, due to the fact that the femoral 1 and tibial 3 elements are pre-formed in different dimensions, they simplify the implantation step of the same in the joint site, as they do not require further shaping operations or modifications of their dimensions for being it possible to adapt them to the size of the bone ends, thereby reducing the time required to perform the surgery.

Moreover, due to the presence of posterior lobes or condylar portions with a substantially straight terminal section or in any case with a large radius of curvature, it is possible to easily extract the femoral element from a respective mold.

This is clearly not possible according to the prior art, such as the spacer device taught by WO2018015878A1, which has rear lobes which are of such configuration as not to allow an easy extraction from a respective production mold.

The possibility of pre-adding or adding to the spacer device using pharmacological and/or therapeutic products then allows to treat local infections in the joint site and to reach the optimal conditions for the implantation of a new joint prosthesis.

Changes and variants of the invention are possible within the scope defined by the claims.

The invention claimed is:

1. A femoral element for a spacer device for a knee joint, said femoral element being designed to be constrained to a femoral bone and having a substantially "C" plan configuration, wherein each free end of the "C" delimits a condylar portion or posterior lobe of said femoral element, said femoral element having a first articulation surface facing, in use, towards a tibial element for articulating said femoral element on or with a tibial element, and a second surface opposite thereto for attachment to a femoral bone,
wherein said first articulation surface has, at a rear or at each posterior lobe or condylar portion, a terminal section opening or extending up to a free or terminal edge of said posterior lobe or condylar portion, said terminal section being straight by having parallel inner and outer walls and extending so as to be, in use, parallel to a craniocaudal axis, or inclined with respect to the craniocaudal axis, or said terminal section being curved and having a radius of curvature at least 50% larger than a radius of curvature of an adjacent and subsequent section of the first articulation surface.

2. The femoral element according to claim 1, wherein said terminal section is straight and is parallel to a front plane, or lies in the front plane, or defines an angle between 0 and 10° or between 0 and 5° or between 0 and 3° with the front plane.

3. The femoral element according to claim 1, wherein said terminal section extends from the free or terminal edge of each condylar portion for an extension equal to at least 60% of the condylar portion.

4. The femoral element according to claim 1, wherein said terminal section extends from the free or terminal edge of the condylar portions for an extension equal to about mm.

5. The femoral element according to claim 1, wherein each condylar portion has the free or terminal edge with an upper, in use, surface, which is straight and has a main extension dimension parallel to a latero-lateral axis.

6. The femoral element according to claim 1, wherein said first surface is convex and has, in a sagittal plane or in a plane parallel thereto, a snail-shaped curved profile with a front section having a first radius of curvature, at least one central section having a second radius of curvature larger than the first radius of curvature, and then at least one rear section having a third radius of curvature smaller than the first and the second radius of curvature.

7. The femoral element according to claim 6, wherein a distance along or parallel to a sagittal axis of a center of rotation of the first radius of curvature from a center of rotation of the second radius of curvature is equal to about 1-3 mm.

8. The femoral element according to claim 6, wherein a distance along or parallel to a craniocaudal axis of a center of rotation of the first radius of curvature from a center of rotation of the second radius of curvature is approximately 2-6 mm.

9. The femoral element according to claim 6, wherein a distance along or parallel to the sagittal axis of a center of rotation of the first radius of curvature from a center of rotation of the third radius of curvature is approximately 15-20 mm.

10. The femoral element according to claim 6, wherein a distance along or parallel to a craniocaudal axis of a center of rotation of the first radius of curvature from a center of rotation of the third radius of curvature is approximately 20-26 mm.

11. The femoral element according to claim 6, wherein said first radius of curvature is equal to about 35-45 mm.

12. The femoral element according to claim 6, wherein said second radius of curvature is equal to about 40-50 mm.

13. The femoral element according to claim 6, wherein said third radius of curvature is equal to about 10-15 mm.

14. The femoral element according to claim 1, wherein at said second surface at least one recessed area is delimited that is designed to facilitate an adhesion of the femoral element to a corresponding femoral bone end, using a filling or constraining material or fluid.

15. The femoral element according to claim 14, wherein said at least one recessed area is open toward a respective side, medial or lateral, of the femoral element so as to facilitate an escape of the fluid, used for constraining to the corresponding femoral bone, that is applied in excess.

16. The femoral element according to claim 1, wherein said second surface of the femoral element is concave and, in a sagittal plane or in a plane parallel thereto, has a curved, U-shaped profile comprising at least an anterior section curved or with rectilinear thicknesses inclined or curved with respect to a craniocaudal axis, then an intermediate or base section parallel to a sagittal axis, and subsequently a posterior section parallel or inclined with respect to the craniocaudal axis.

17. A spacer device comprising:
a femoral element designed to be constrained to a femoral bone and having a "C" plan configuration, wherein each free end of the "C" delimits a condylar portion or posterior lobe of said femoral element, said femoral element having a first articulation surface facing, in use, towards a tibial element for articulating said femoral element on or with the tibial element, and a second surface opposite to the first articulation surface for attachment to a femoral bone, said first articulation surface having, at a rear or at each posterior lobes or condylar portion, a terminal section opening or extending up to a free or terminal edge of said posterior lobe or condylar portions said terminal section being straight by having parallel inner and outer walls and extending so as to be, in use, parallel to a craniocaudal axis or inclined with respect to the craniocaudal axis, or said terminal section being curved with a radius of curvature at least 50% larger than a radius of curvature of an adjacent and subsequent section of the first surface, and the tibial element configured to be constrained to a tibial bone, at one end of the tibial bone facing a knee joint, the tibial element comprising a first surface facing, in use, towards the femoral element and designed to articulate or engage with said first articulation surface of said femoral element and a second surface opposite to the first articulation surface and for constraint to the tibial bone.

* * * * *